(12) United States Patent
Mori et al.

(10) Patent No.: US 10,023,897 B2
(45) Date of Patent: Jul. 17, 2018

(54) BIOSENSOR CHIP, AND BIOSENSOR DEVICE EQUIPPED WITH SAME

(71) Applicant: Panasonic Healthcare Co., Ltd., Ehime (JP)

(72) Inventors: Kazuyoshi Mori, Ehime (JP); Masahiro Kouge, Ehime (JP); Fumihisa Kitawaki, Ehime (JP); Takako Matsumura, Ehime (JP); Seiji Onishi, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 163 days.

(21) Appl. No.: 14/501,848

(22) Filed: Sep. 30, 2014

(65) Prior Publication Data

US 2015/0024477 A1 Jan. 22, 2015

Related U.S. Application Data

(63) Continuation of application No. PCT/JP2013/002989, filed on May 9, 2013.

(30) Foreign Application Priority Data

May 16, 2012 (JP) .................................. 2012-112167
May 16, 2012 (JP) .................................. 2012-112168
(Continued)

(51) Int. Cl.
*C12Q 1/04* (2006.01)
*G01N 35/00* (2006.01)
(Continued)

(52) U.S. Cl.
CPC .......... *C12Q 1/04* (2013.01); *B01L 3/502738* (2013.01); *B01L 3/527* (2013.01);
(Continued)

(58) Field of Classification Search
CPC ................... C12Q 1/04; B01L 2200/16; B01L 2300/0864; B01L 2300/0867;
(Continued)

(56) References Cited

U.S. PATENT DOCUMENTS 7,435,381 B2    10/2008  Pugia et al.
2004/0241042 A1 12/2004  Pugia et al.
(Continued)

FOREIGN PATENT DOCUMENTS

EP    2329877 A1 *  6/2011  ............ B01F 1/0027
JP    2006-308366    11/2006
(Continued)

OTHER PUBLICATIONS

Focke et al., "microstructuring of polymer films for sensitive genotyping by real-time PCR on a centrifugal microfluidic platform, Lab chip, 2010, 10, 2519-2526".*
(Continued)

*Primary Examiner* — Michael L Hobbs
*Assistant Examiner* — Liban M Hassan
(74) *Attorney, Agent, or Firm* — Wenderoth, Lind & Ponack, L.L.P.

(57) ABSTRACT

A biosensor chip is placed in a biosensor device and is rotated while a biochemical analysis specimen is measured, the biosensor chip comprising a main body, a holding chamber, a dispensing chamber, a plurality of quantification chambers, and a plurality of measurement chambers. The main body has an inlet into which the specimen is poured. The holding chamber holds the poured specimen inside the main body. The dispensing chamber is connected to the holding chamber via a first channel and dispenses the specimen. The quantification chambers are connected to the dispensing chamber, hold a specific amount of the dispensed specimen, and are disposed at positions located away from
(Continued)

a rotational center of a rotary motion according to a distance from the first channel. The measurement chambers are connected to the quantification chambers via a second channel and react the specimen with a biochemical analysis reagent.

3 Claims, 17 Drawing Sheets

(30) Foreign Application Priority Data

| Nov. 2, 2012 | (JP) | 2012-242425 |
|---|---|---|
| Nov. 2, 2012 | (JP) | 2012-242426 |
| Nov. 2, 2012 | (JP) | 2012-242427 |

(51) Int. Cl.
*B01L 3/00* (2006.01)
*G01N 33/487* (2006.01)

(52) U.S. Cl.
CPC .... *G01N 35/00029* (2013.01); *B01L 2200/04* (2013.01); *B01L 2200/0605* (2013.01); *B01L 2200/16* (2013.01); *B01L 2300/042* (2013.01); *B01L 2300/043* (2013.01); *B01L 2300/0816* (2013.01); *B01L 2300/0864* (2013.01); *B01L 2300/0867* (2013.01); *B01L 2400/0409* (2013.01); *B01L 2400/0633* (2013.01); *B01L 2400/0677* (2013.01); *G01N 33/487* (2013.01); *G01N 2035/00158* (2013.01)

(58) Field of Classification Search
CPC .. B01L 2400/0409; B01L 3/502; B01L 3/527; B01L 3/502738; B01L 2200/04; B01L 2200/0605; B01L 2300/042; B01L 2300/043; B01L 2300/0816; B01L 2400/0633; B01L 2400/0677; G01N 21/07; G01N 33/487; G01N 35/00029; G01N 2035/00158

USPC .......... 435/288.7, 45, 586.1, 294.1; 422/68.1
See application file for complete search history.

(56) References Cited

U.S. PATENT DOCUMENTS

| 2006/0245972 | A1 | 11/2006 | Osone et al. |
|---|---|---|---|
| 2007/0003433 | A1 | 1/2007 | Horike et al. |
| 2009/0041627 | A1 | 2/2009 | Pugia et al. |
| 2009/0143250 | A1* | 6/2009 | Lee ................... B01L 3/502738 506/39 |
| 2010/0009431 | A1 | 1/2010 | Cho et al. |
| 2010/0086990 | A1 | 4/2010 | Stanley et al. |
| 2010/0158757 | A1 | 6/2010 | Horiike et al. |

FOREIGN PATENT DOCUMENTS

| JP | 2007-500850 | 1/2007 |
|---|---|---|
| JP | 2007-24851 | 2/2007 |
| JP | 2007-333716 | 12/2007 |
| JP | 2008-281500 | 11/2008 |
| JP | 4336834 | 9/2009 |
| JP | 2010-25854 | 2/2010 |
| JP | 2010-519892 | 6/2010 |
| JP | 2011-527753 | 11/2011 |
| WO | 2008/106719 | 9/2008 |

OTHER PUBLICATIONS

Stumpf et al. "Centrifugal microfluidic system for primary amplification and secondary real-time PCR, lab chip, 2010, 10, 3210-3212".*
Oosterbroek et al., "EP2329877A1, Machine Translation", translated on Dec. 13, 2016.*
Office Action dated Jun. 7, 2016 in Japanese patent application No. 2012-242425.
International Search Report dated Aug. 13, 2013 in International (PCT) Application No. PCT/JP2013/002989.

* cited by examiner

BIOSENSOR CHIP, AND BIOSENSOR DEVICE EQUIPPED WITH SAME

CROSS-REFERENCE TO RELATED APPLICATIONS

This is a continuation application under 35 U.S.C. 120 and 35 U.S.C. 365 of International Application PCT/JP2013/002989, with an international filing date of May 9, 2013 which claims priority to Japanese Patent Applications No. 2012-112167 and No. 2012-112168 filed on May 16, 2012 and No. 2012-242425, No. 2012-242426 and No. 2012-242427 filed on Nov. 2, 2012. The entire disclosures of PCT/JP2013/002989 and Japanese Patent Applications No. 2012-112167, No. 2012-112168, No. 2012-242425, No. 2012-242426 and No. 2012-242427 are hereby incorporated herein by reference.

BACKGROUND

Technical Field

The present invention relates to a biosensor chip that is used in the detection of bacteria, viruses, and so forth that can cause a variety of infectious diseases, and to a biosensor device equipped with this chip.

Description of the Related Art

In the past, biosensor chips of this type have been used in devices that perform nucleic acid amplification reaction, for example, in the analysis of objects included in a specimen.

A conventional biosensor chip internally comprised a main body case having a diluent chamber and a measurement chamber connected via a first channel to this diluent chamber, an inlet provided to a portion of this main body case corresponding to the diluent chamber, and a sealing member for sealing this inlet. The measurement chamber had a branching chamber component that was connected to the diluent chamber via the first channel, and a plurality of individual measurement components connected to this branching chamber component via second channels. Individual reagents were provided to the individual measurement components (see Japanese Unexamined Patent Application Publication (Translation of PCT Application) No. 2010-519892, for example).

With the prior art discussed above, an example of biological information is the identification of the presence or type of a virus. In the case of the common cold, for example, the strain (that is, the form of the virus) changes every year. To detect that virus, it is necessary to house individual reagents for detecting the virus in individual measurement components, to house a different individual reagent for each individual measurement component, and to combine a plurality of types of individual reagents.

However, there are hundreds of individual reagents corresponding to viruses that must be combined in a plurality of types for the purpose of detection, and these combinations have to be taken into account and numerous biosensor chips prepared. Accordingly, the management of so many biosensor chips in which individual reagents of different types are combined entailed a tremendous expense, and this drove up the cost.

Moreover, with a conventional configuration, when individual reagents of different types were applied and dried under the same environment, there was the risk that cross contamination between the individual reagents would occur, and this could lead to decreased measurement accuracy.

In view of this, it is an object of the present invention to prevent a decrease in measurement accuracy caused by contamination, and to thereby lower the cost.

SUMMARY

The biosensor chip pertaining to the first invention is a biosensor chip that is placed in a biosensor device and is rotated while a specimen is measured, the biosensor chip comprising a main body, a holding chamber, a dispensing chamber, a plurality of quantification chambers, and a plurality of measurement chambers. The main body has an inlet into which a biochemical analysis specimen is poured. The holding chamber holds the poured specimen inside the main body. The dispensing chamber is connected to the holding chamber via a first channel and dispenses the specimen. The plurality of quantification chambers are connected to the dispensing chamber, hold a specific amount of dispensed specimen, and are disposed at positions located away from the rotational center of the rotary motion according to the distance from the first channel. The plurality of measurement chambers are connected to the quantification chambers via a second channel and react the specimen with a biochemical analysis reagent.

In a configuration in which this biosensor chip is placed in a biosensor device and rotated, of the plurality of quantification chambers, the farther away a quantification chamber is disposed from the first channel, the farther it is disposed away from the rotational center of the rotary motion. Thus, the quantification chambers empty of specimen starting from the side closest to the first channel, so specimen is successively supplied to the adjacent quantification chamber disposed downstream in the rotational direction.

Consequently, a specific amount of specimen can be introduced into the plurality of quantification chambers, and the amount of specimen held in the quantification chambers can be kept from becoming inconsistent, which happens when specimen flows backward from an adjacent quantification chamber.

Also, with a chip configuration in which an overflow chamber is provided on the downstream side of the plurality of quantification chambers in the rotational direction, if waves should be produced in the specimen in the overflow chamber as a result of fluctuation in the rotary speed of the rotary motion, backflow of the specimen in the overflow chamber can be prevented in the same way as when lower waves cannot quite reach a higher bank. As a result, the various quantification chambers can be kept in a state in which the specified amount of specimen has been introduced, so the proper analysis can be performed, using a consistent amount of specimen, in the measurement chambers into which the specimen is supplied from these quantification chambers.

DETAILED DESCRIPTION OF THE PREFERRED EMBODIMENTS

The biosensor chip pertaining to an embodiment the present invention will now be described through reference to the drawings.

Embodiment 1

Figure 1:
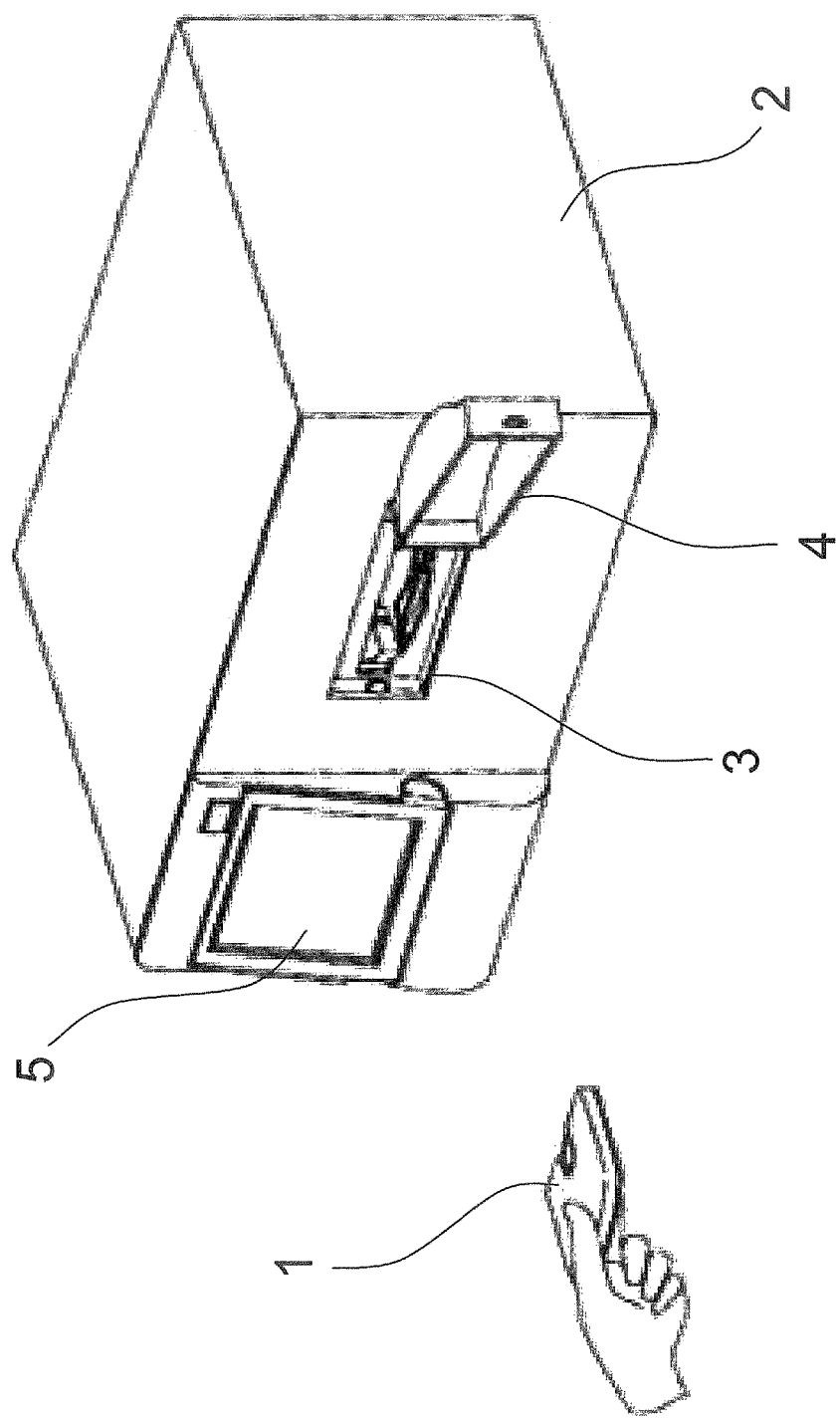
FIG. 1 is an oblique view of a biosensor device featuring the biosensor chip pertaining to Embodiment 1 of the present invention.

FIG. 1 is an example of a biosensor device, and shows a biosensor device that detects the influenza virus and identifies the strain, as an example of biological information collected from a patient.

Biosensor Device

As shown in FIG. 1, the biosensor device in this embodiment comprises a biosensor chip 1 in which an influenza specimen is housed, a device main body 2, an opening 3 for inserting the biosensor chip 1 into the device main body 2, a lid 4 for closing the opening 3, and a display component 5 that is provided to the face where the opening 3 is formed, and that displays detection results.

Figure 2:
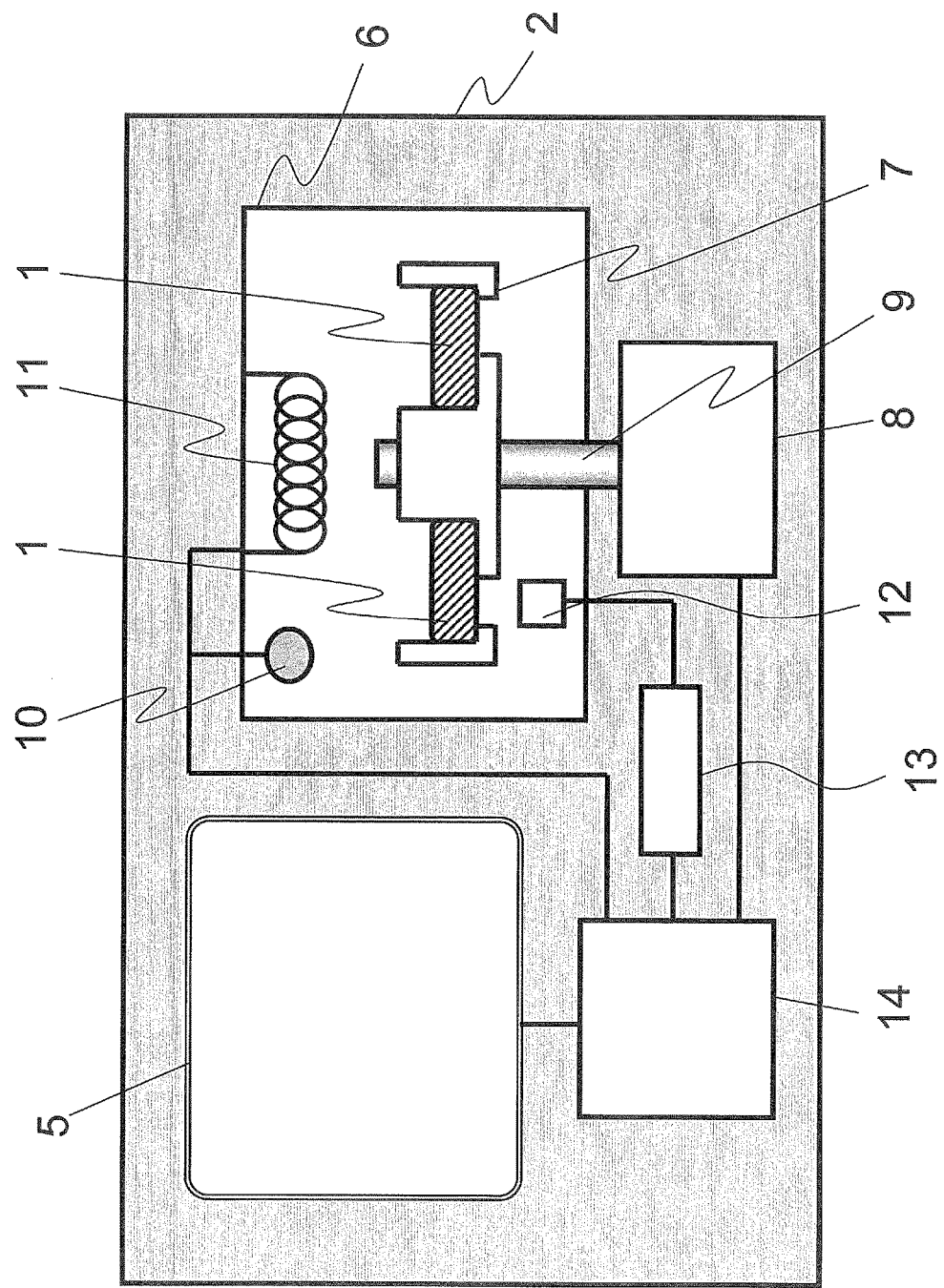
FIG. 2 is a diagram of the configuration of the biosensor device pertaining to Embodiment 1 of the present invention.

As shown in FIG. 2, a space 6 that communicates with the opening 3 is formed in the interior of the device main body 2. A rotary tray 7 for fixing the biosensor chip 1 is disposed in the space 6.

The rotary tray 7 is connected at its center part to a shaft connected to a rotation mechanism 8, and is rotated by the rotation mechanism 8.

A temperature sensor 10 is disposed at the top inside the space 6.

The temperature sensor 10 is provided in order to monitor the temperature inside the space 6, and the temperature in the space 6 can be adjusted to a specific temperature by switching on or off a heater 11 disposed in the space 6, on the basis of the temperature sensed by the temperature sensor 10.

An optical sensor 12 is then disposed on the bottom face of the rotary tray 7, opposite the lower face of the biosensor chip 1, in the space 6.

The optical sensor 12 senses an influenza specimen on the biosensor chip 1.

Also disposed in the interior of the device main body 2 are a computer 13 that computes values sensed by the optical sensor 12, and a controller 14 that controls the biosensor device.

With the above configuration, in this embodiment, a plurality of individual specimens that react with a plurality of types of virus are housed in the biosensor chip 1 in order to sense the type of influenza specimen.

Biosensor Chip 1

Figure 3:
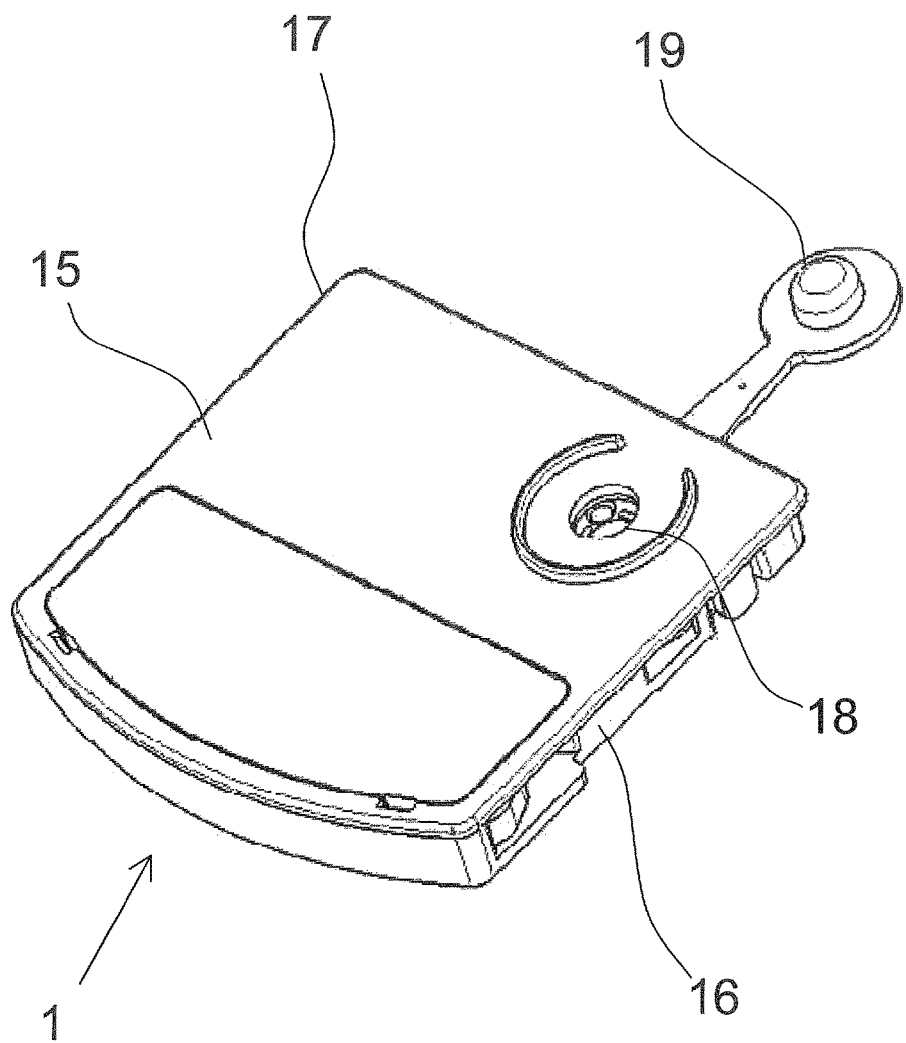
FIG. 3 is an oblique view of the biosensor chip pertaining to Embodiment 1 of the present invention.

As shown in FIG. 3, the biosensor chip 1 comprises main body case 17 constituted by putting together a substantially square cover 15 and a substantially square base 16.

The cover 15 has an inlet 18 for introducing a specimen at one corner of the substantially square shape.

Figure 4:
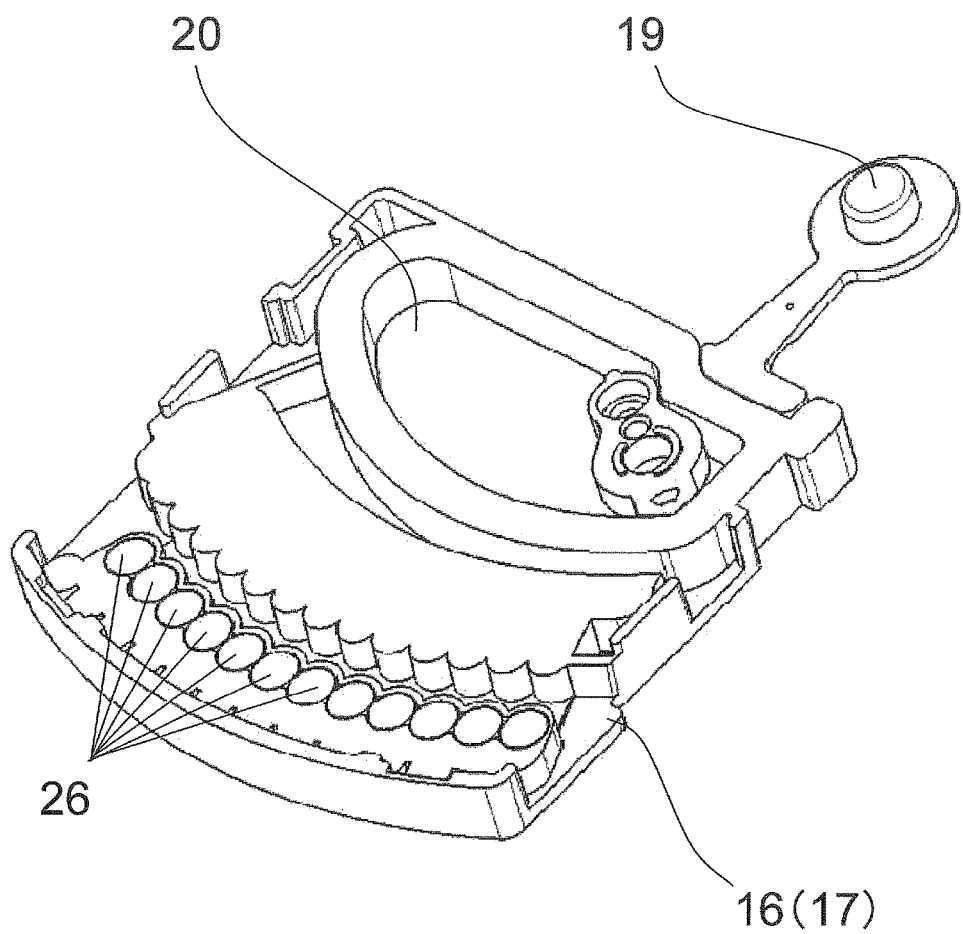
FIG. 4 is an oblique view of the interior on the inlet side of the biosensor chip pertaining to Embodiment 1 of the present invention.

The inlet 18 is sealed off by a sealing member 19. As shown in FIG. 4, a diluent chamber 20 that communicates with the inlet 18 is provided to the portion of the main body case 17 on the inlet 18 side.

A diluent is housed ahead of time in the diluent chamber 20. In the state in FIG. 3, a seal (not shown) is affixed over the inlet 18 so that the diluent will not flow out of the inlet 18.

Therefore, when an influenza specimen is poured out of the inlet 18, first this seal is peeled off, and then the influenza specimen is poured from the inlet 18 into the diluent chamber 20. Consequently, the influenza specimen and the diluent are mixed together, and a diluted specimen of a specific concentration is held in the diluent chamber 20.

Figure 5:
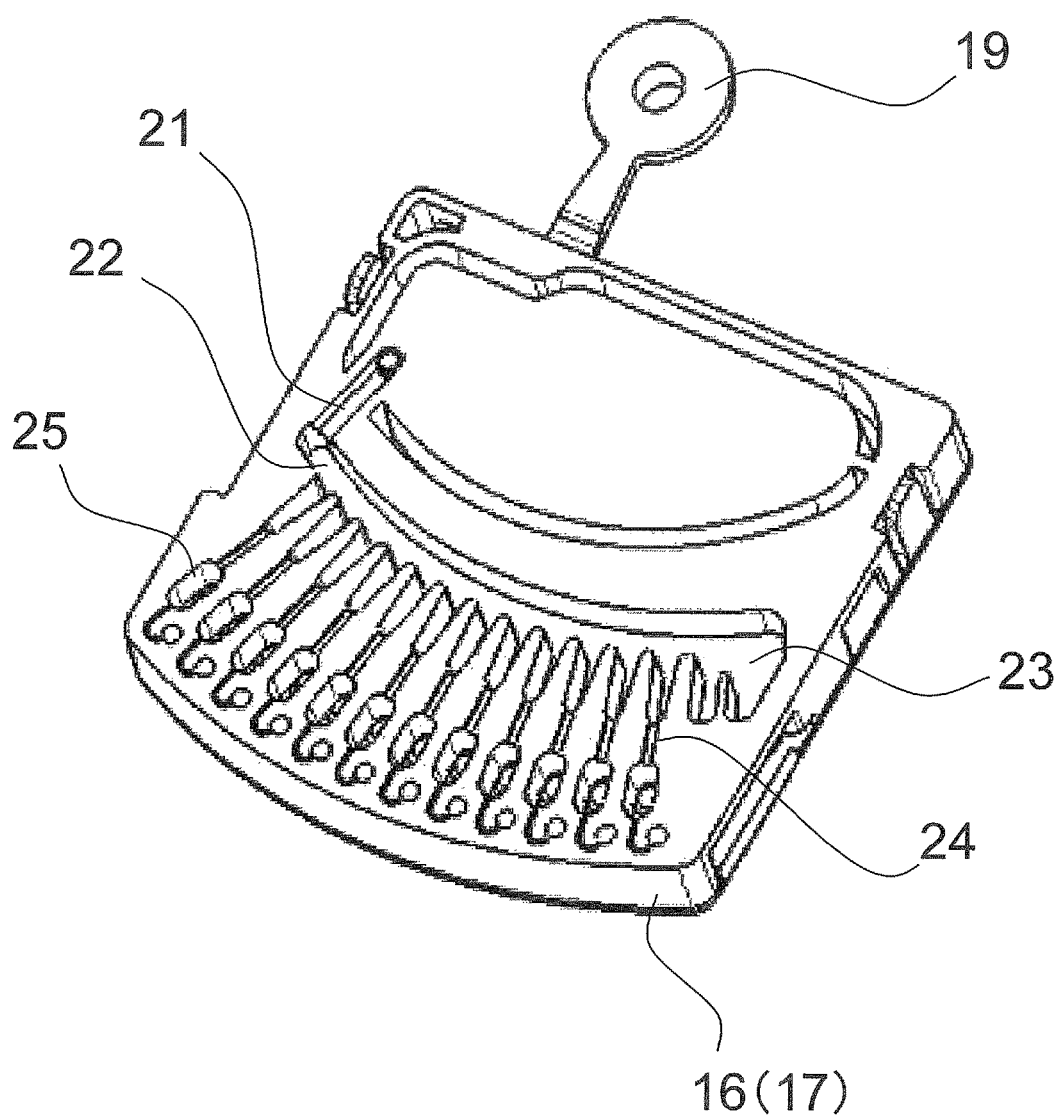
FIG. 5 is an oblique view of the interior on the opposite side from the inlet side of the biosensor chip pertaining to Embodiment 1 of the present invention.
Figure 6:
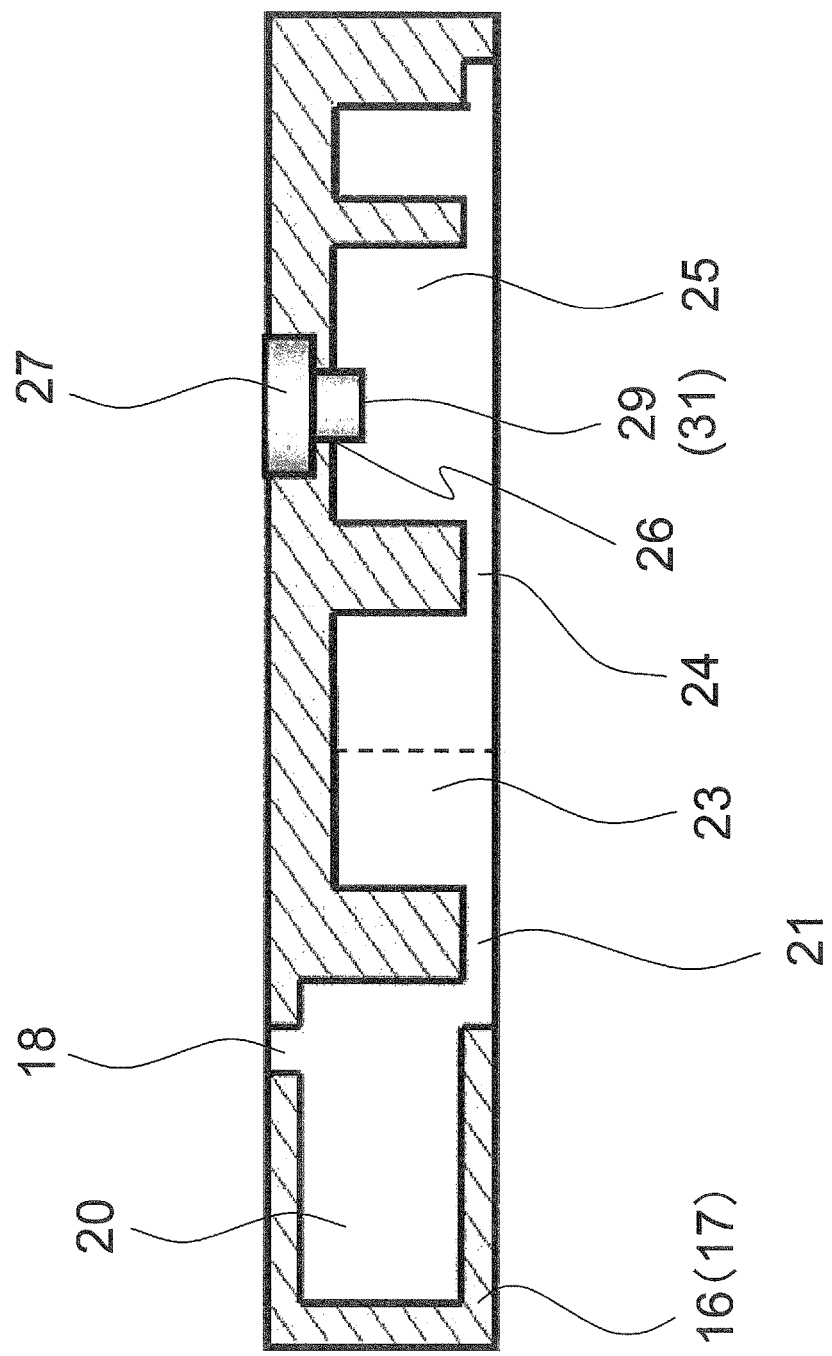
FIG. 6 is a cross section of the portion where diluted specimen flows in the biosensor chip pertaining to Embodiment 1 of the present invention.

As shown in FIGS. 5 and 6, a measurement chamber 22 that is linked via a first channel 21 to the diluent chamber 20 is provided inside the main body case 17 (more precisely, to the base 16).

The measurement chamber 22 has a branched chamber 23 that is linked via the first channel 21 to the diluent chamber 20, and a plurality of individual measurement chambers 25 that are connected via second channels 24 to the branched chamber 23.

Figure 7A:
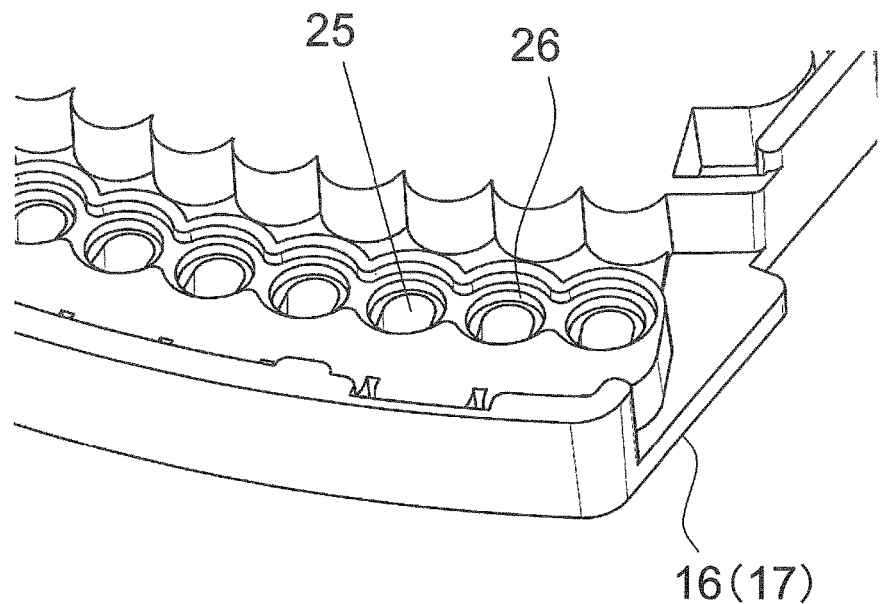
FIG. 7A is an oblique view of a state in which there is no cap on the individual measurement components in the biosensor chip pertaining to Embodiment 1 of the present invention.
Figure 7B:
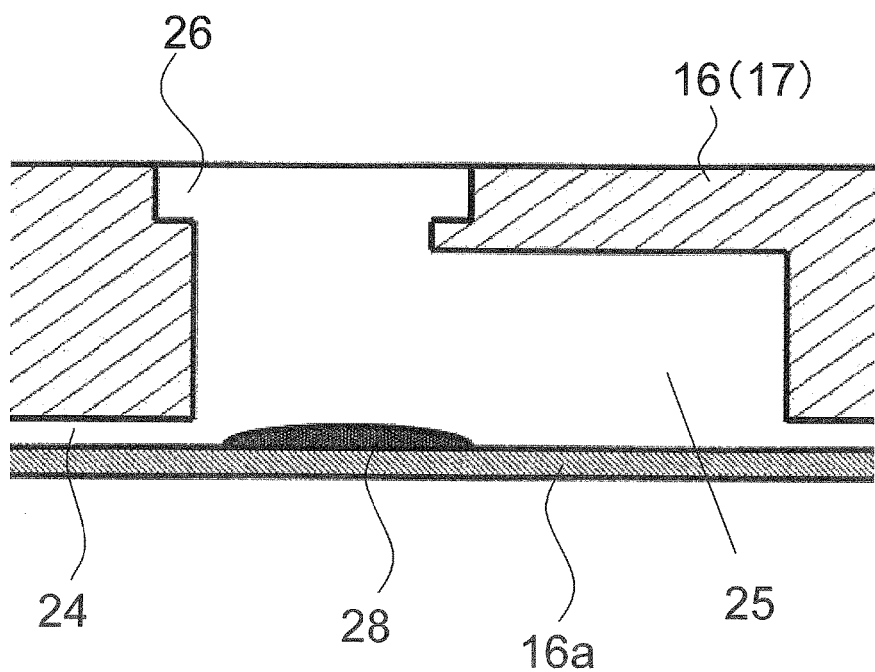
FIG. 7B is a cross section of a state in which there is no cap on the individual measurement components in the biosensor chip pertaining to Embodiment 1 of the present invention.

As shown in FIG. 6, the individual measurement chambers 25 have a plurality of reagent mounting holes 26 on the face of the main body case 17 where the inlet 18 is formed, that is, at the base 16 portion on the cover 15 side. Also, caps 27 that hold different kinds of individual reagents are removably mounted to the reagent mounting holes 26. As shown in FIGS. 7A and 7B, the individual measurement chambers 25 have a common reagent 28 that reacts with a plurality of types of specimen, on the bottom face opposite the reagent mounting holes 26.

The mounting of the common reagent 28 will now be described in greater detail through reference to FIGS. 7A and 7B.

First, as shown in FIG. 7A, a plurality of the reagent mounting holes 26 are formed on the upper face side of the base 16 constituting the main body case 17, that is, on the cover 15 side where the inlet 18 is formed. As shown in FIG. 7B, a film 16a is provided on the lower face side of the base 16, that is, on the face opposite the reagent mounting holes 26.

The film 16a constitutes the individual measurement chambers 25 along with the base 16.

As shown in FIG. 5, the individual measurement chambers 25 have a rectangular shape disposed along the radial direction, with the inlet 18 at the center. As shown in FIGS. 7A and 7B, the individual measurement chambers 25 are linked to the second channels 24 on the film 16a side. The individual measurement chambers 25 are also linked to the branched chamber 23 via the second channels 24. The liquid common reagent 28 is dropped through the reagent mounting holes 26 onto the film 16a and dried, and this holds the common reagent 28 in the individual measurement chambers 25.

The common reagent 28 is essential to the detection of bacteria and viruses, and performs the job of amplifying a specimen that is present in the diluted specimen. Therefore, individual reagents 29 that react individually with the bacterium or virus to be detected needs to be separately held in the individual measurement chambers 25.

Figure 8A:
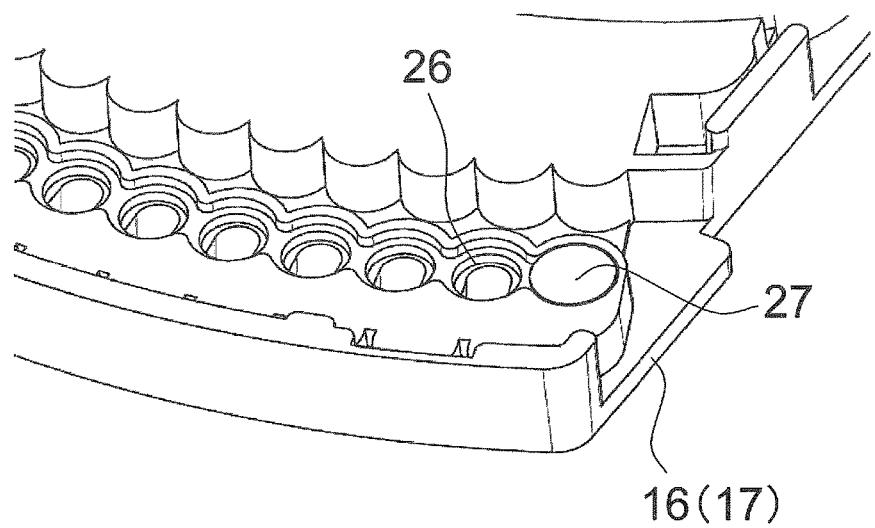
FIG. 8A is an oblique view of a state in which there is a cap on an individual measurement component in the biosensor chip pertaining to Embodiment 1 of the present invention.
Figure 8B:
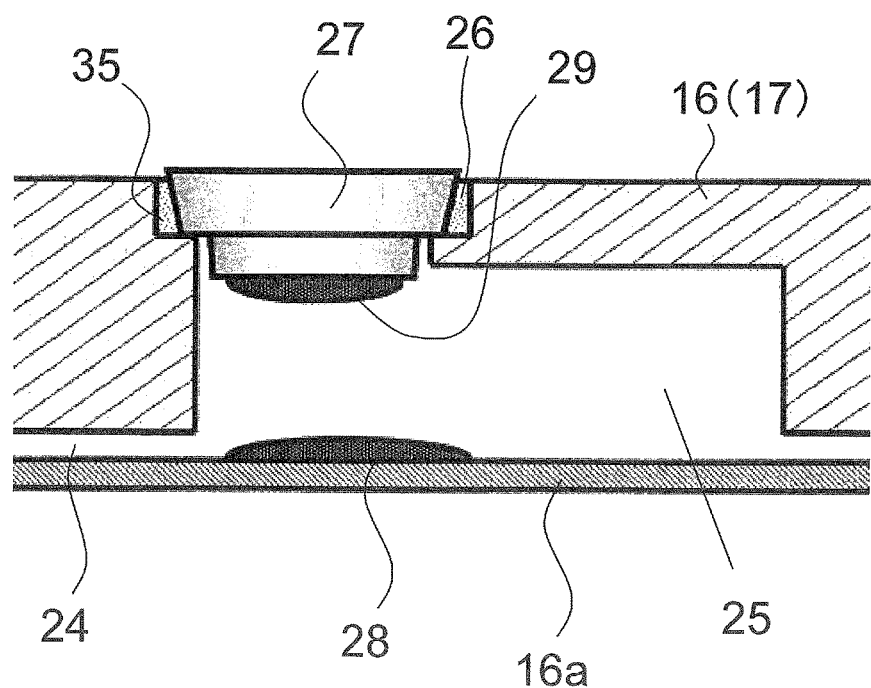
FIG. 8B is a cross section of a state in which there is a cap on an individual measurement component in the biosensor chip pertaining to Embodiment 1 of the present invention.

In view of this, in this embodiment, as shown in FIGS. 8A and 8B, the individual reagents 29 are held in the plurality of caps 27 mounted to the reagent mounting holes 26.

Figure 9:
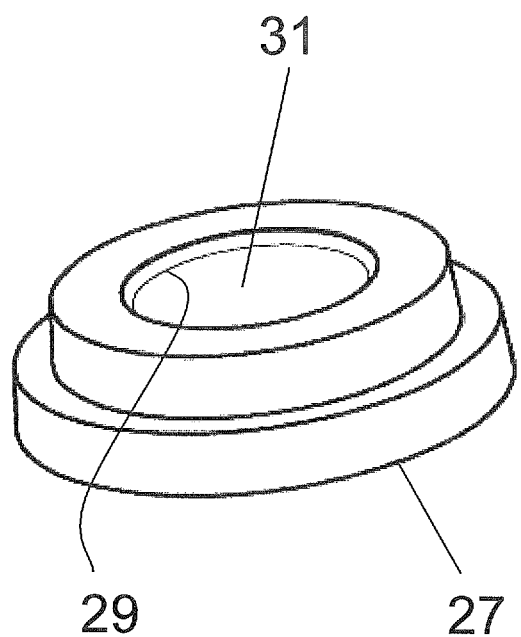
FIG. 9 is an oblique view of the cap pertaining to Embodiment 1 of the present invention.

As shown in FIG. 9, the caps 27 have a substantially cylindrical shape, and a circular recess is formed in the inner face of each of the individual measurement chambers 25.

The liquid individual reagents 29 are dropped into the interior of the recesses 31 and then dried, which fixes the individual reagents 29. The recesses 31 are substantially bowl shaped, and the surface tension of the liquid causes the individual reagents 29 to dry and be fixed in a state in which they are uniformly spread out over the inner peripheral face of the recesses 31.

As shown in FIG. 8A, the caps 27 to which the individual reagents 29 have been fixed can be attached to the reagent mounting holes 26, preparing individual reagents 29 of different types that have been fixed for the various reagent mounting holes 26. Consequently, when there are individual reagents 29 corresponding to a plurality of types of strain, such as strain A or B, as with an influenza virus, when the specimen is detected, the caps 27 to which the different individual reagents 29 have been fixed can be attached to the individual measurement chambers 25, allowing the user to ascertain which specimens in a single detection reacts with which individual reagents 29.

That is, individual reagents 29 of different types can be fixed to the caps 27 mounted to adjacent individual measurement chambers 25, and measurement performed. This makes it easy to sense the strain of an influenza virus, for example.

As shown in FIG. 8B, the caps 27 is fixed with an adhesive agent 35 to the circular reagent mounting holes 26. Therefore, the caps 27 will not come loose even if subjected to an external force, such as centrifugal force. Furthermore, the portion of the caps 27 coated with the adhesive agent 35 is the exterior part of the individual measurement chambers 25 in a state in which the caps 27 have been mounted to the reagent mounting holes 26. Consequently, the adhesive agent 35 does not reach the individual reagents 29 inside the individual measurement chambers 25. That is, the recesses 31 are provided to keep the adhesive agent 35 coating the caps 27 from covering the surface of the individual reagents 29 and hampering the reaction thereof The recesses 31 are also formed so as to be surrounded by an annular bank.

Incidentally, a specimen collected from a patient will undergo a favorable reaction with the individual reagent 29 at around 60° C. If the temperature were considerably lower than 60° C., the reaction would take a long time, but if the temperature were considerably higher than 60° C., the specimen itself would be destroyed and there would be no reaction. Accordingly, the diluted specimen must flow into the individual measurement chambers 25 while the interior of the individual measurement chambers 25 is held at 60° C.

In view of this, with the biosensor chip 1 in this embodiment a heat-fusible sealing material that fills in the space inside the second channels 24 is provided.

The heat-fusible sealing material used here is one that will melt at approximately 40° C. Consequently, in the course of heating the individual measurement chambers 25 of the biosensor chip 1 to 60° C., the heat-fusible sealing material of the second channels 24 begins to melt, and spaces in which the diluted specimen moves are formed inside the second channels 24.

Consequently, the diluted specimen held in the branched chamber 23 can flow into the individual measurement chambers 25 under the centrifugal force produced by the biosensor chip 1 during the rotation of the rotary tray 7. As a result, the spaces inside the individual measurement chambers 25 can be maintained at about 60° C.

If the introduction of the heat-fusible sealing material into the second channels 24 is performed while using a dispenser, for example, and monitoring through the reagent mounting holes 26 in a state in which the caps 27 have not yet been mounted to the reagent mounting holes 26 in FIGS. 8A and 8B, then this introduction can be easily accomplished by drawing the molten heat-fusible sealing material under the capillary action of the second channels 24.

With the configuration of the biosensor chip 1 in this embodiment, a diluted specimen is introduced into the individual measurement chambers 25 to which the individual reagents 29 have been mounted, and is subjected to an amplification reaction. This amplification reaction is detected by the optical sensor 12, which confirms which specimen is reacting with the individual reagents 29. This result is displayed on the display component 5.

With this embodiment, as discussed above, the individual reagents 29 necessary for detection are provided on the faces of the caps 27 exposed inside the individual measurement chambers 25. A configuration is employed that allows the caps 27 to be mounted to the reagent mounting holes 26 of the individual measurement chambers 25.

Consequently, the main body case 17 may be managed as a shared part, and the caps 27 may be appropriately selected and mounted according to the individual applications of the virus or the like to be detected. As a result, production costs, management costs, and other such costs can be greatly reduced.

Also, since the caps 27 are smaller than the main body case 17, even when a plurality of caps 27 are managed, they can be simply managed in a small amount of space. This also affords a cost reduction.

The biosensor chip 1 is also such that the caps 27 holding the individual reagents 29 can be mounted in the reagent mounting holes 26 of the individual measurement chambers 25. Accordingly, since the individual reagents 29 are held in the small caps 27 that afford easy environment management such as cleanliness ahead of time, contamination of the individual reagents 29 can be prevented. As a result, this avoids the adverse effects on measurement accuracy that would otherwise be caused by contamination of the individual reagents 29, and allows for more accurate measurement.

When different types of the individual reagents 29 are applied and dried under the same environment, there is the risk of contamination between the individual reagents 29.

In this embodiment, the individual reagents 29 are housed on the caps 27 apart from the main body case 17. Thus, the individual reagents 29 can be applied and dried in isolated spaces, and this prevents contamination between the individual reagents 29.

Also, even if it is necessary to house the common reagent 28 and the individual reagents 29 in a separated state in the individual measurement chambers 25 in order to avoid deactivation of the reagents, in this embodiment reagent deactivation can be easily prevented by housing the individual reagents 29 in the caps 27, and the common reagent 28 in the individual measurement chambers 25 of the main body case.

The film 16a that seals the individual measurement chambers 25 is generally formed from a plastic film or the like, and is bonded to the main body case 17 by heat sealing or another such means. Accordingly, if a reagent has low heat resistance, there is the risk that it will end up being deactivated by this heat.

In this embodiment, since there are reagent mounting holes 26 that communicate with the respective individual measurement chambers 25, the film 16a can be bonded to the main body case 17 by heat sealing, and the film 16a can then be coated with the common reagent 28 through the reagent mounting holes 26. This effectively prevents deactivation of the common reagent 28 as well.

Embodiment 2

In this embodiment, those components that are shared with Embodiment 1 above will be numbered the same, and these components will not be described in detail again.

FIG. 1 is an example of a biosensor device, and shows a biosensor device that detects an influenza virus.

In this embodiment, just as in Embodiment 1 above, the biosensor chip 1 into which influenza specimens have been introduced is inserted into the biosensor device shown in FIG. 1. A biosensor chip 1 is inserted into the interior of a device main body 2 through an opening 3 formed in the device main body 2 of the biosensor device. The device main body 2 of the biosensor device is also provided with a lid 4 for blocking off the opening 3, a display component 5 for displaying detection results, and so forth.

That is, the biosensor chip 1 is placed inside the device main body 2 of the biosensor device, and the result of biochemical analysis is displayed on the display component 5.

Figure 10:
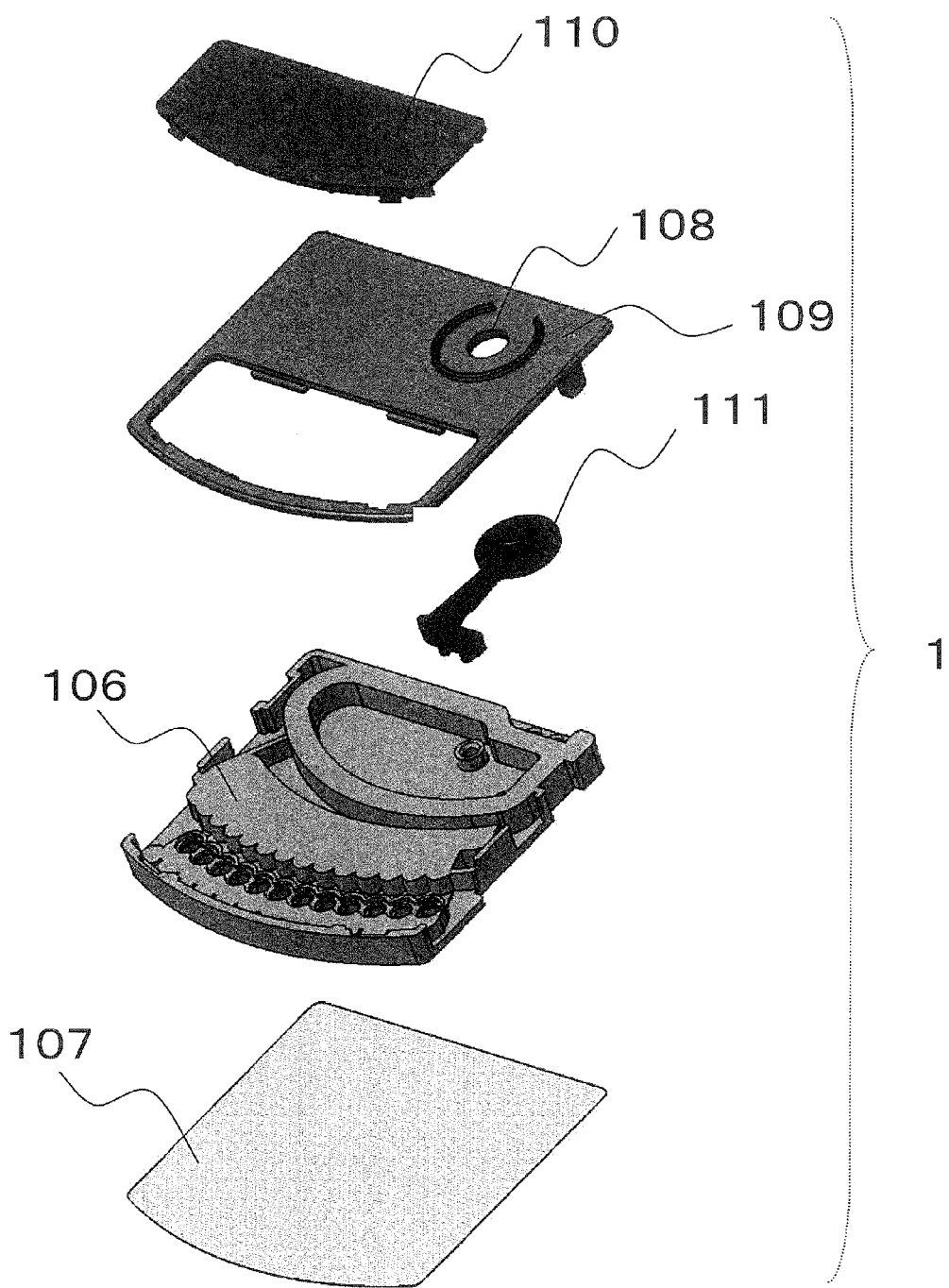
FIG. 10 is an oblique view of a biochemical analysis biosensor chip pertaining to Embodiment 2 of the present invention.

As shown in FIG. 10, the biosensor chip 1 that performs this biochemical analysis comprises a chip main body 106, a lower cover 107, an inlet 108, an upper cover 109, an accessory cover 110, and a sealing member 111.

The chip main body 106 has in its interior a holding chamber 112 (discussed below), a dispensing chamber 114, quantification chambers 115, measurement chambers 117, and so forth (see FIG. 11, etc.).

The lower cover 107 is attached to the lower face of the chip main body 106.

The inlet 108 is attached to the upper face of the chip main body 106, and specimens used for biochemical analysis are introduced into this inlet.

The inlet 108 is formed in the upper cover 109.

The accessory cover 110 is attached to the upper face of the upper cover 109.

The sealing member 111 seals the inlet 108.

The configuration of this chip main body 106 will now be described in detail.

Figure 11:
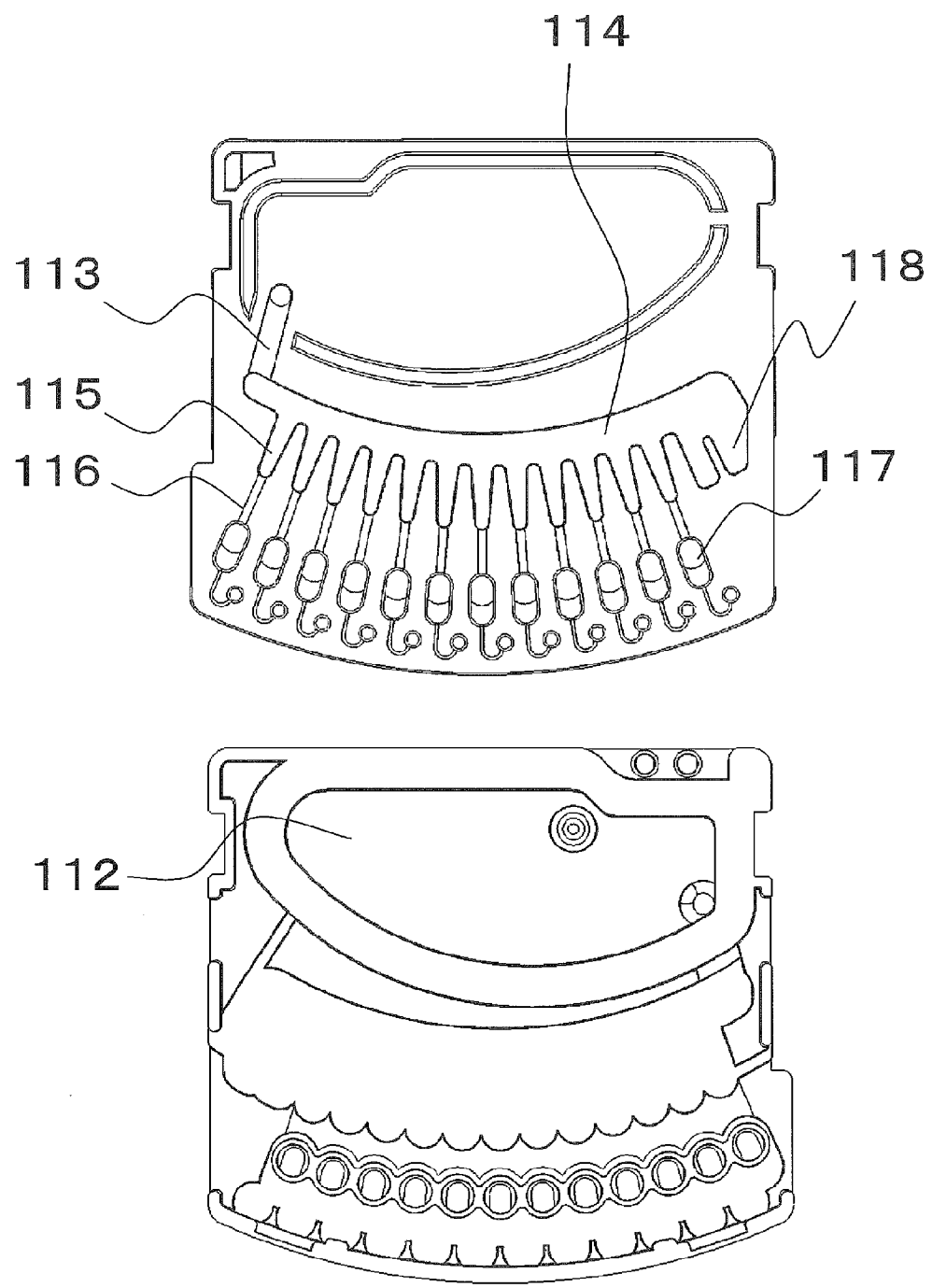
FIG. 11 consists of plan views of the biosensor chip pertaining to Embodiment 2 of the present invention.

As shown in FIG. 11, the chip main body 106 has in its interior the holding chamber 112, the dispensing chamber 114, a plurality of the quantification chambers 115, and a plurality of the measurement chambers 117.

The holding chamber 112 holds the introduced specimen.

The dispensing chamber 114 is connected via a first channel 113 to the holding chamber 112, and dispenses specimens.

The quantification chambers 115 are connected to the dispensing chamber 114, and hold the dispensed specimens.

The measurement chambers 117 are connected to the respective quantification chambers 115 via second channels 116, and react the specimens with the biochemical analysis reagents.

The reagents used in this embodiment are applied as a coating to the interior of the measurement chambers 117 ahead of time.

As shown in FIG. 11, an overflow chamber 118 is formed at a position that is farther away from the first channel 113 than the quantification chambers 115. In other words, the overflow chamber 118 is provided on the downstream side of the quantification chambers 115 in the rotational direction of the biosensor chip 1.

The overflow chamber 118 holds any specimen that has overflowed from the quantification chambers 115.

In this embodiment, when the biosensor chip 1 undergoes rotary motion after being placed in the biosensor device, of the plurality of quantification chambers 115, the quantification chambers 115 located away from the first channel 113 are disposed at positions farther away from the rotational center of the rotary motion than the quantification chambers 115 located closer to the first channel 113.

Figure 12:
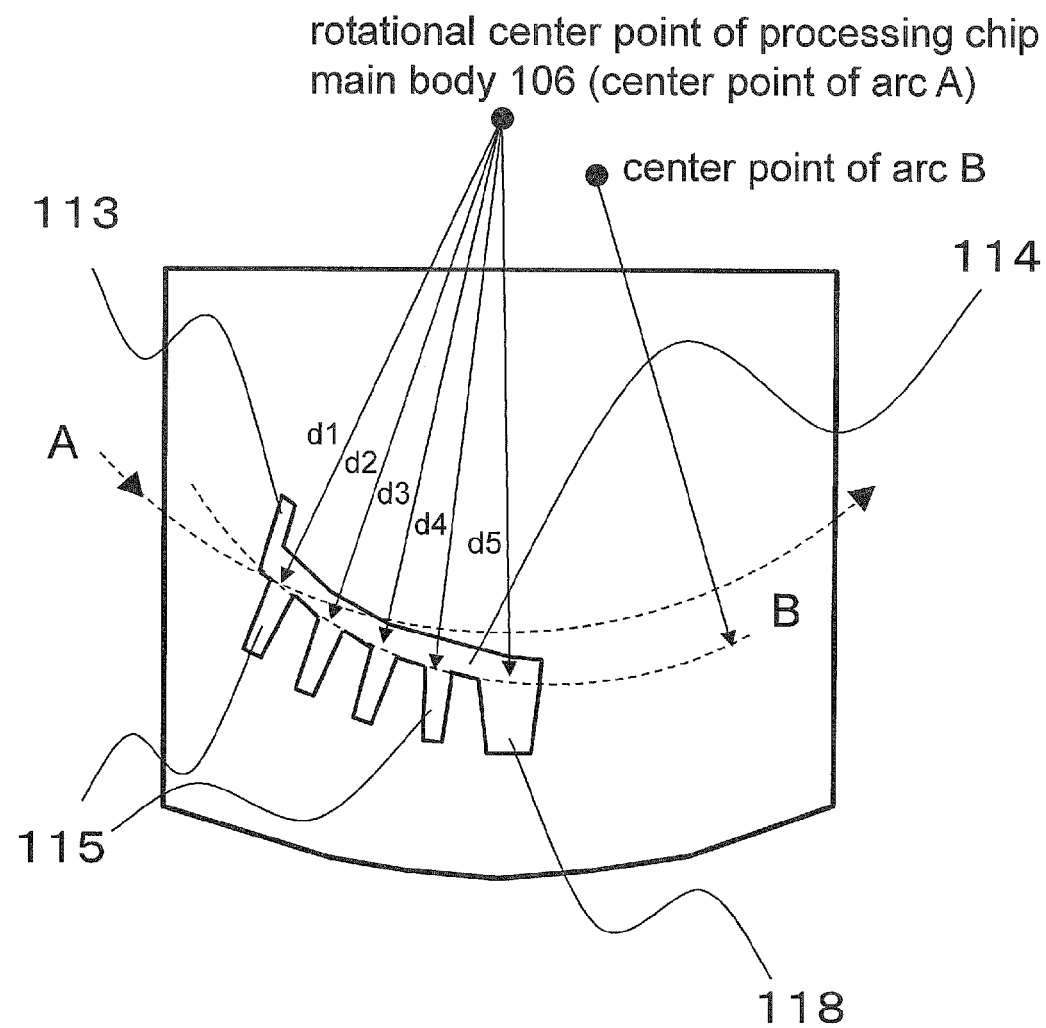
FIG. 12 is a complement to a plan view of the biosensor chip pertaining to Embodiment 2 of the present invention.

More precisely, as shown in FIG. 12, the quantification chambers 115 are disposed so that the distances (d1 to d4) from the rotational center of the chip main body 106 are separated in stages such that d1<d2<d3<d4.

For example, as shown in FIG. 12, the quantification chambers 115 are farther away from the first channel 113 than the rotational center of the chip main body 106 (the center point of an arc A), and are disposed on an arc B whose center point is located on the inside in the radial direction with respect to the arc A.

As shown in FIG. 12, the shape of the dispensing chamber 114 is substantially fan shaped in plan view, and of the two ends thereof, the length in the radial direction of the first end closer to the first channel 113 is shorter than the length in the radial direction of the second end farther away from the first channel 113.

The above-mentioned radial direction lengths of the first and second ends refer to the lengths in the radial direction of a fan shape whose center is the rotational center of the chip main body 106.

Consequently, specimens are successively supplied to the quantification chambers 115 disposed on the downstream side in the rotational direction as they are emptied of specimens starting from the quantification chambers 115 closest to the first channel 113 side.

Consequently, the specified amount of specimen can be introduced into the quantification chambers 115, so the proper analysis can be carried out.

The overflow chamber 118 is provided at the farthest downstream point in the rotational direction of the quantification chambers 115. Therefore, backflow of the specimen from the overflow chamber 118 to the quantification chamber 115 side can be prevented during rotary motion. As a result, the amount of specimen held in the quantification chambers 115 can be stabilized, and the proper analysis can be carried out.

That is, in this embodiment, specimens are supplied from the holding chamber 112, through the dispensing chamber 114 and the quantification chambers 115, to the measurement chambers 117 by rotating the chip main body 106 that has been placed in the biosensor device.

Here, in order to promote a reaction between the reagents and the specimens in the measurement chambers 117, the rotational speed of the chip main body 106 is sometimes changed to agitate the specimens and the reagents. This change in the rotational speed can create waves in the specimen in the overflow chamber 118, and there is the risk that these will flow back into the quantification chambers 115.

In view of this, in this embodiment the quantification chambers 115 are disposed at locations that are distant from the rotational center of the rotary motion of the chip main body 106 according to the distance from the first channel 113.

Consequently, even if waves should be generated in the specimen in the overflow chamber 118 by a change in rotational speed, the specimen can be prevented from flowing backward in the same way as when lower waves cannot quite reach a higher bank. As a result, the various quantification chambers 115 can be kept in a state in which the specified amount of specimen has been introduced. Accordingly, the amount of specimen held in the measurement chambers 117 to which specimens are supplied from the quantification chambers 115 can be stabilized, so the proper analysis can be performed.

The overflow chamber 118 is disposed so that the distance d5 from the rotational center of the chip main body 106 to the distance d4 of the adjacent measurement chamber 115 will be d4<d5. This allows any specimen that has overflowed from the quantification chambers 115 to be stably introduced into the overflow chamber 118.

Furthermore, once specimen has flowed into the overflow chamber 118, it is prevented from flowing back to the measurement chambers 115 located on the upstream side in the rotational direction.

As a result, the specified amount of specimen can be stably held in the quantification chambers 115, and the proper analysis can be conducted.

Embodiment 3

In this embodiment, those components that are shared with Embodiment 1 above will be numbered the same, and these components will not be described in detail again.

The configuration shown in FIGS. 1 and 2 is the same as in Embodiment 1 above, and therefore will not be described again here.

With the above configuration, in this embodiment a biosensor chip 1 that detects an influenza virus and also identifies the strain will be described in detail as an example of biological information about a specimen collected from a patient's nostrils.

As shown in FIGS. 13A to 14b, the biosensor chip 1 comprises a diluent chamber 216 and a main body case 219 that has in its interior measurement chambers 218 that are linked to the diluent chamber 216 via a channel 217.

The main body case 219 has an inlet 220 at the portion corresponding to the diluent chamber 216. The inlet 220 is sealed from the outside of the main body case 219 by a sealing member 221.

Figure 13A:
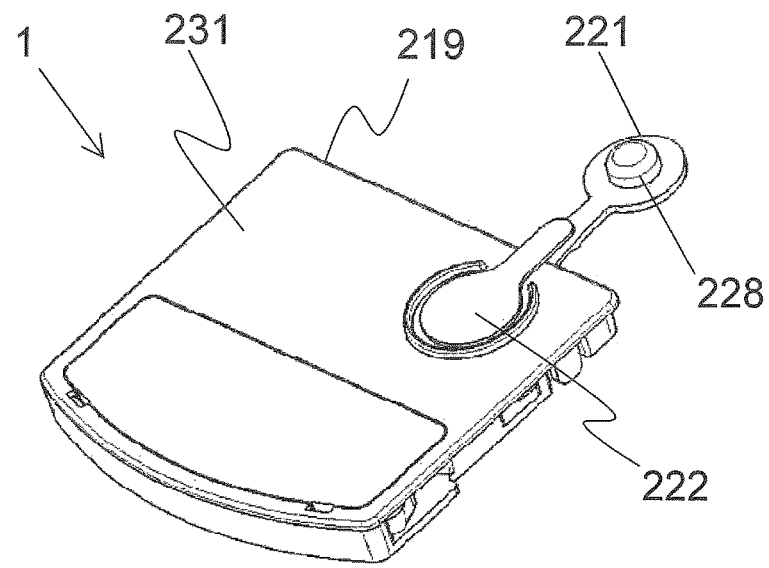
FIG. 13A is an oblique view of when there is an inlet seal on the biosensor chip pertaining to Embodiment 3 of the present invention.

As shown in FIG. 13A, a seal 222 is affixed to the inlet 220 of the biosensor chip 1 before the specimen is introduced, in order to keep any contamination or the like that would hinder measurement from flowing into the interior of the diluent chamber 216.

Figure 14A:
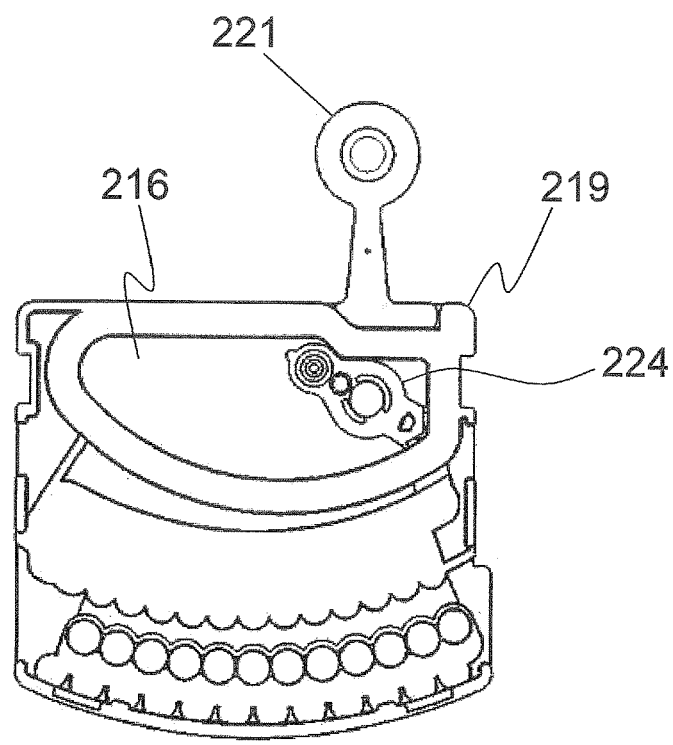
FIG. 14A is an internal configuration diagram of the biosensor chip pertaining to Embodiment 3 of the present invention, as seen from the inlet side.
Figure 14B:
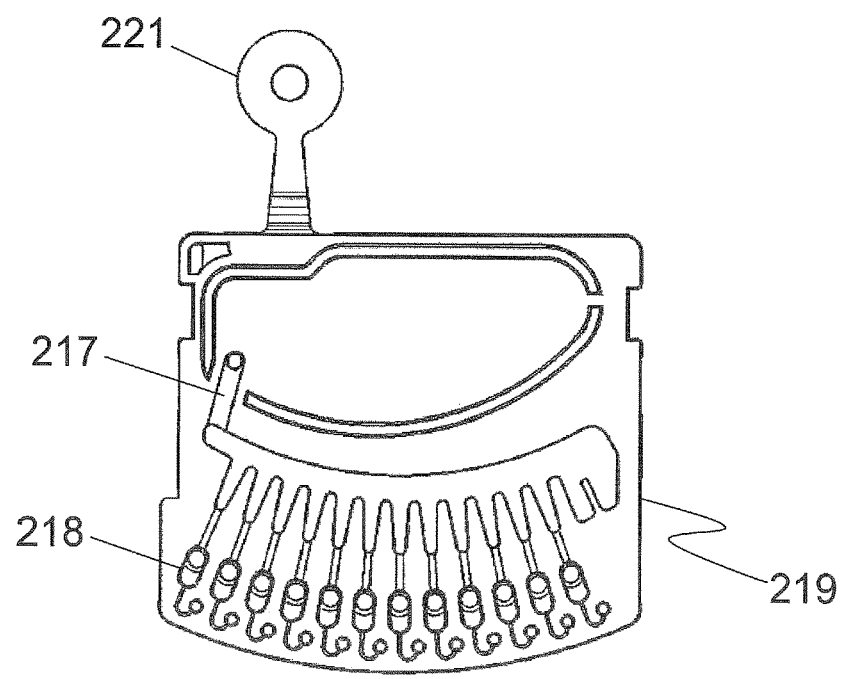
FIG. 14B is an internal configuration diagram of the biosensor chip pertaining to Embodiment 3 of the present invention, as seen from the opposite side from the inlet side.

A diluent for diluting a specimen is sealed in the interior of the diluent chamber 216. As shown in FIGS. 14A and 15A sealing member 224 is disposed in the interior of the diluent chamber 216 in order to keep the diluent from flowing into the measurement chambers 218 until just before specimen detection is performed.

Figure 15:
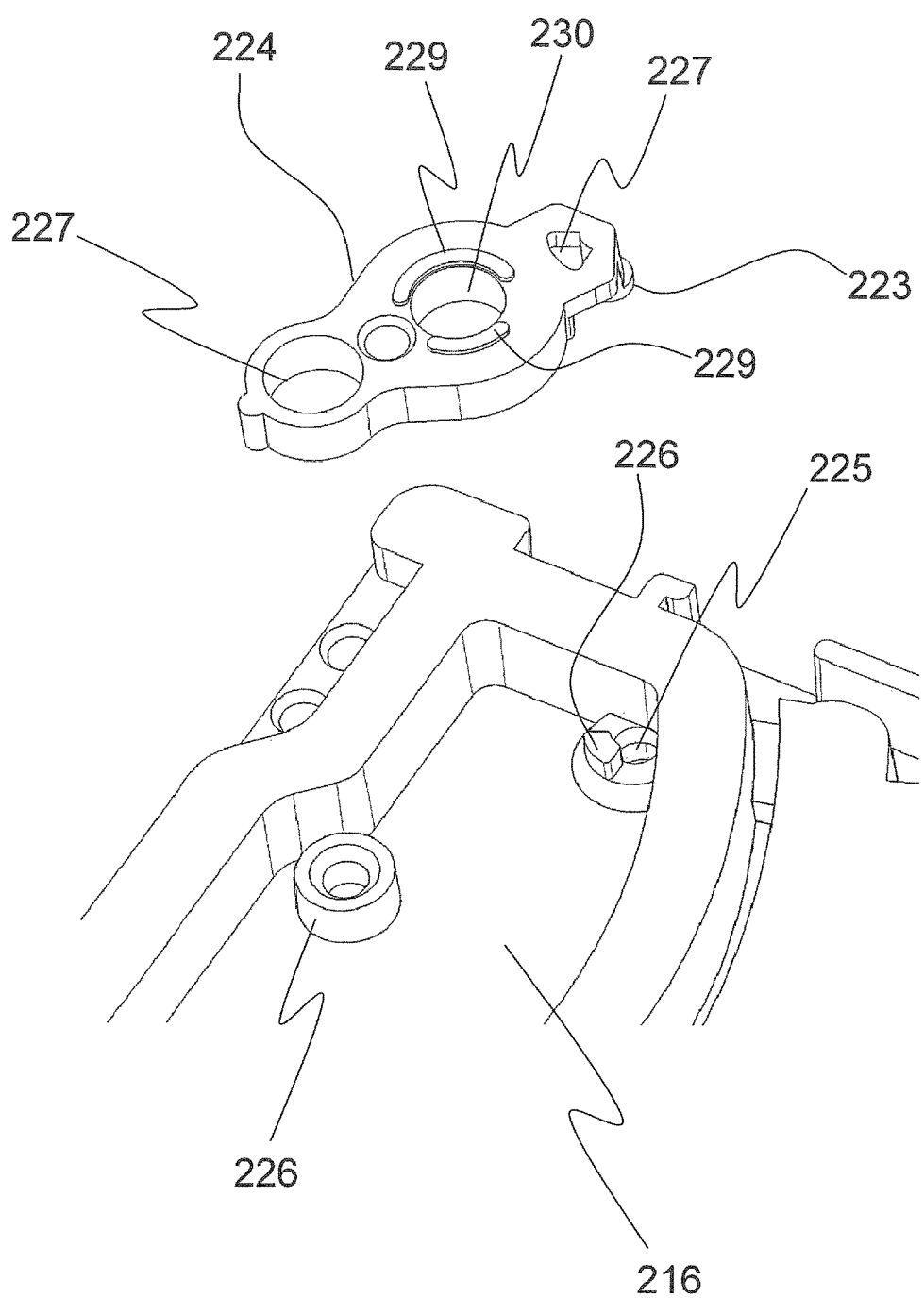
FIG. 15 is an exploded oblique view of the attached state of a sealing member of the biosensor chip pertaining to Embodiment 3 of the present invention.

As shown in FIG. 15, the sealing member 224 has through-holes 227 formed in both ends in the lengthwise direction. A support column 226 that supports the sealing member 224 provided in the diluent chamber 216 movably in the axial direction is inserted into a through-hole 227. This allows the sealing member 224 to move downward in the drawing along the axial direction of the support column 226 within the diluent chamber 216.

Figure 16A:
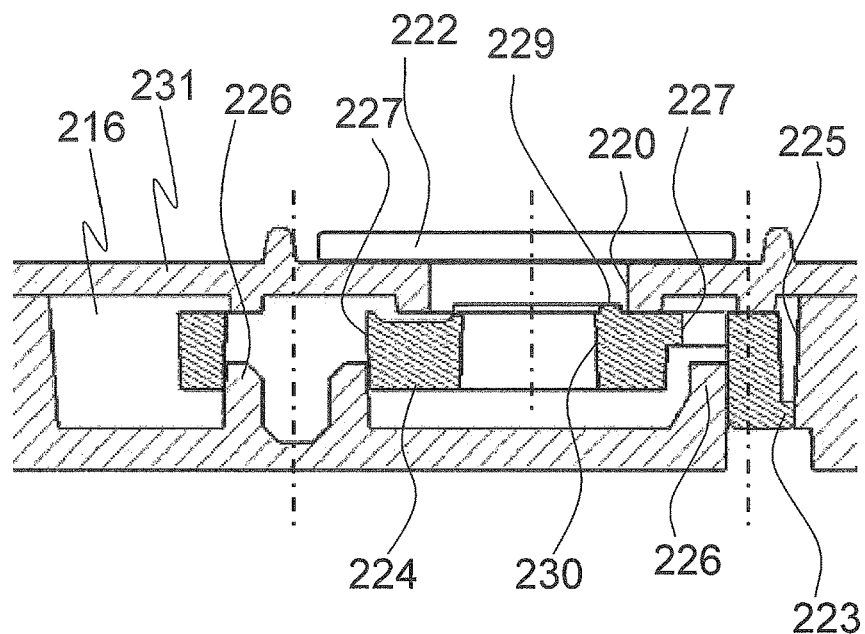
FIG. 16A is an I-II cross section of the state prior to sealing with the sealing member of the biosensor chip in FIG. 13B.

FIG. 16A shows the state before the inlet 220 is sealed by the sealing member 221.

As shown in FIG. 16A, the sealing member 224 is disposed in a state in which a sealing component 223 seals an opening 225 side of the channel 217. After the sealing member 224 is disposed in the diluent chamber 216, the diluent chamber 216 is sealed by a cover 231. As shown in FIG. 13A, the inlet 220 is sealed by the seal 222.

Figure 13B:
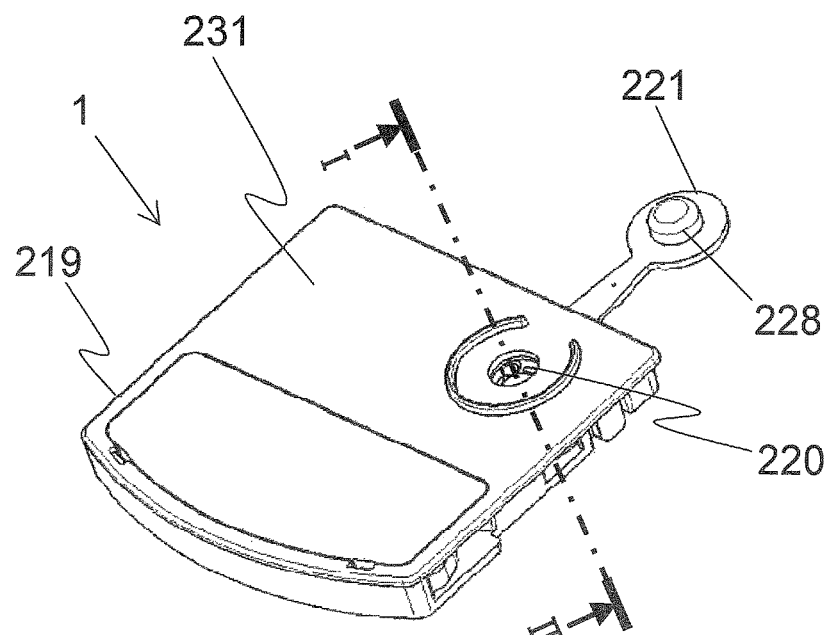
FIG. 13B is an oblique view of when there is no inlet seal on the biosensor chip pertaining to Embodiment 3 of the present invention.

Then, as shown in FIG. 13B, the seal 222 is removed to open up the inlet 220, and in this state a specimen collected with a pipette or the like is introduced into the diluent chamber 216.

The specimen here is moved in and out of the diluent chamber 216 through the inlet 220 from and into the pipette, which mixes the introduced specimen with the diluent and results in a mixture of consistent concentration.

Once the introduction of the specimen into the biosensor chip 1 is thus complete, the user seals off the inlet 220 with the sealing member 221.

Figure 16B:
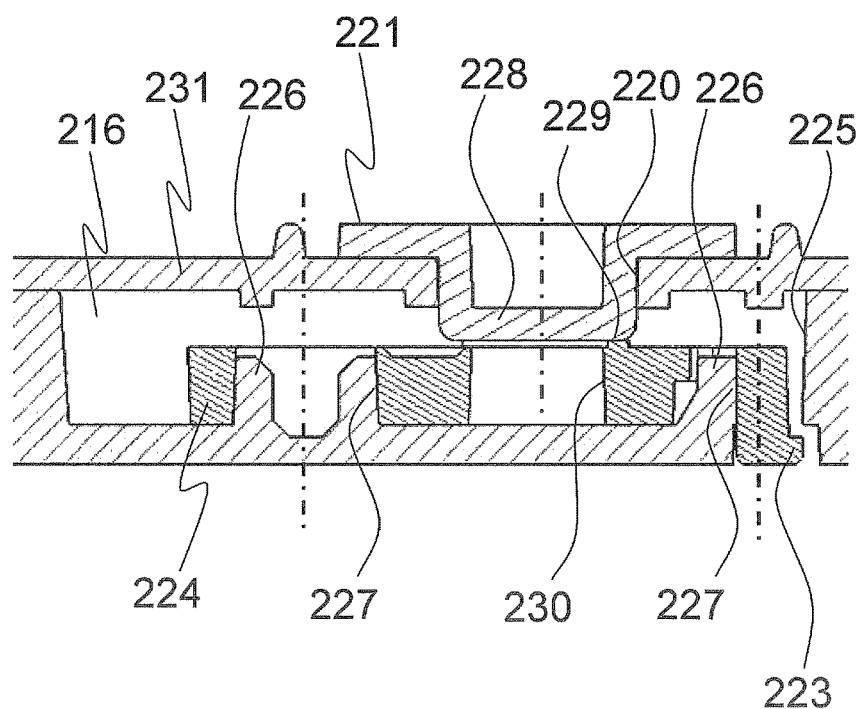
FIG. 16B is an I-II cross section of the state after sealing with the sealing member of the biosensor chip in FIG. 13B.

As shown in FIG. 16B, a protrusion 228 is formed on the sealing member 221. The outside diameter of the protrusion 228 is greater than the inside diameter of the inlet 220. Furthermore, the material of the cover 231 in which the inlet 220 is formed is harder than the material of the sealing member 221 having the protrusion 228.

Accordingly, when the sealing member 221 is pushed into the inlet 220, the sealing member 221 undergoes elastic deformation as it is pushed into the inlet 220. In this state, the sealing member 221 is unlikely to come loose from the inlet 220.

As shown in FIG. 15, pressure receivers 229 are provided along the outer peripheral edge on the inlet 220 side end of a biological inlet 230 formed in the sealing member 224. The pressure receivers 229 hit the protrusion 228 when the sealing member 221 is inserted into the inlet 220.

That is, as shown in FIG. 16B, the sealing member 224 disposed in the diluent chamber 216 is such that the protrusion 228 of the sealing member 221 hits the pressure receivers 229, and is pushed in toward the interior of the diluent chamber 216 from the inlet 220 side.

The inside diameter of the through-hole 227 of the pushed-in sealing member 224 is smaller than the outside diameter of the support column 226 formed in the diluent chamber 216, and the material of the sealing member 224 is harder than the material of the support column 226. Thus, the support column 226 undergoes elastic deformation, making the sealing member 224 less likely to come loose from the support column 226.

The sealing member 224 is formed from a harder material than the cover 231 and the support column 226. Accordingly, as shown in FIGS. 15 and 16B, even if the pressure receivers 229 is pushed by the sealing member 221 so that the sealing member 224 is press-fitted and fixed to the support column 226, the sealing member 224 will be fixed to the support column 226 without bending. Thus, the opening 225 side of the channel 217 is unblocked from the sealing component 223 and left open.

Therefore, the channel 217 between the measurement chambers 218 and the diluent chamber 216 is ensured through the operation of blocking off the inlet 220 with the sealing member 221. Consequently, the mixture of diluent and specimen flows from the diluent chamber 216 into the measurement chambers 218.

The pressure receivers 229 of the sealing member 224 have a substantially circular ring shape that includes cut-outs, around the outer peripheral edge of the biological inlet 230.

Figure 17:
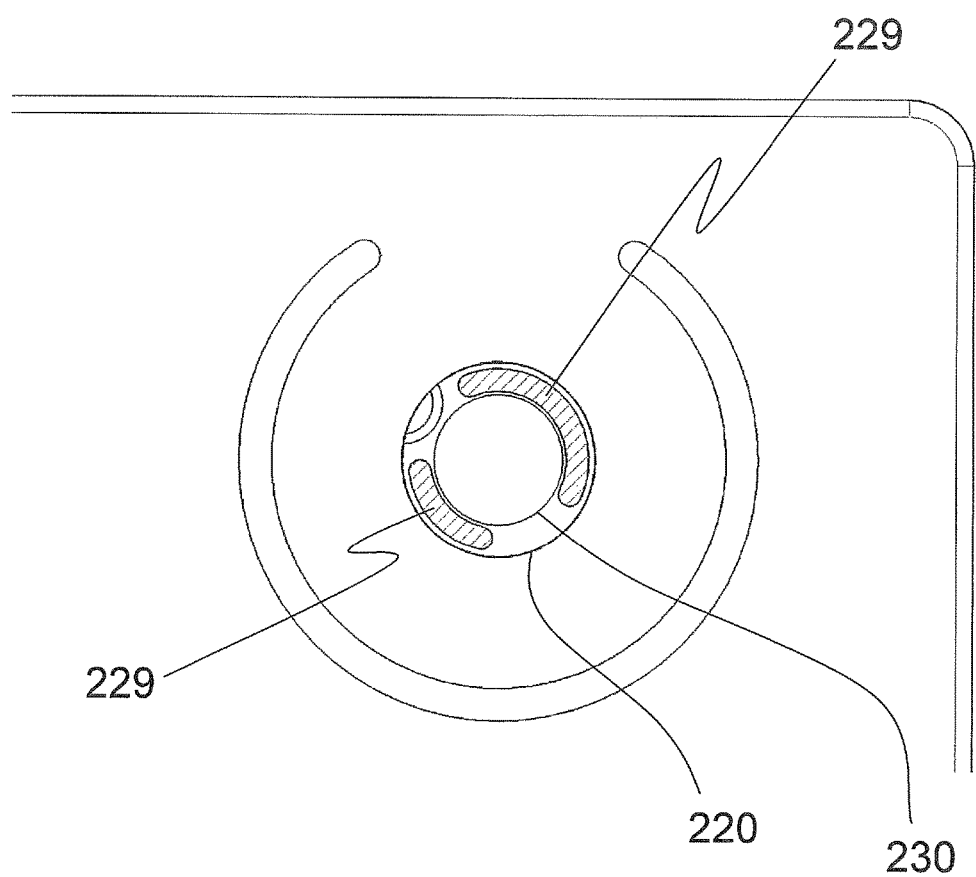
FIG. 17 is a plan view of the inlet in FIG. 13B, as seen from the diluent chamber side.

That is, as shown in FIGS. 15 and 17, the two fan-shaped pressure receiver 229 are formed at the portions other than the cut-outs, with a specific space interposed in the peripheral direction, in order to ensure a gap allowing communication between the biological inlet 230 and the diluent chamber 216 in the direction along a line connecting the two through-holes 227.

Consequently, even when the sealing member 224 is pushed by the protrusion 228 of the sealing member 221 toward the inside of the diluent chamber 216, a flow path can be ensured in which the opening 225 side of the channel 217 and the diluent chamber 216 are always communicating. Thus, a mixture of diluent and specimen can flow into the measurement chambers 218.

In this embodiment, the biosensor chip 1 into which a specimen has been introduced is inserted through the opening 3 of the biosensor device, and placed on the rotary tray 7. The operator then starts the detection process by giving an input to start up the device from the display component 5 of the device main body 2, which causes the biosensor chip 1 to rotate and exerts centrifugal force on the mixture. Consequently, the centrifugal force causes a specific amount of mixture to flow into the measurement chambers 218. The specimen is then sensed by the optical sensor 12, and the result is displayed on the display component 5.

As discussed above, with the biosensor chip 1 in this embodiment, in a state in which the inlet 220 has been sealed off by the sealing member 221, the sealing component 223 that seals the channel 217 moves downward (in the drawing) in the axial direction of the support column 226, and this opens up the channel 217.

Consequently, even if the biosensor chip 1 is accidentally dropped by the user, since the channel 217 is physically sealed by the sealing component 223, no diluent will flow into the measurement chambers 218. As a result, mixing of the diluent and the specimen just prior to use is prevented, and more accurate detection is possible.

INDUSTRIAL APPLICABILITY

The biosensor device pertaining to the present invention effectively prevents contamination and thereby increases measurement accuracy, and also greatly reduces management costs and other such costs.

REFERENCE SIGNS LIST 1 biosensor chip
2 device main body
3 opening
4 lid
5 display component
6 space
7 rotary tray
8 rotation mechanism
9 shaft
10 temperature sensor
11 heater
12 optical sensor
13 computer
14 controller
15 cover
16 base
16a film
17 main body case
18 inlet
19 sealing member
20 diluent chamber
21 first channel
22 measurement chamber
23 branched chamber
24 second channel
25 individual measurement chamber
26 reagent mounting hole
28 common reagent
29 individual reagent
31 recess
35 adhesive agent
106 chip main body
107 lower cover
108 inlet
109 upper cover
110 accessory cover
111 sealing member
112 holding chamber
113 first channel
114 dispensing chamber
115 diluent chamber
116 second channel
117 measurement chamber
118 overflow chamber
206 space
207 rotary tray
208 rotation mechanism
209 shaft
210 temperature sensor
211 heater
212 optical sensor
213 computer
214 controller
216 diluent chamber
217 channel
218 measurement chamber
219 main body case
220 inlet
221 sealing member
222 seal
223 sealing component
224 sealing member 225 opening
226 support column
227 through-hole
228 protrusion
229 pressure receiver
230 biological inlet
231 cover

The invention claimed is:

1. A biosensor chip that is positioned in a biosensor device and is rotated while a biochemical analysis specimen is measured, the biosensor chip comprising:
 a main body having an inlet into which the specimen is poured;
 a holding chamber configured to hold the specimen which has been poured inside the main body;
 a dispensing chamber connected to the holding chamber via a first channel, and configured to dispense the specimen;
 a plurality of quantification chambers including (i) a first quantification chamber connected to the dispensing chamber, configured to hold a specific amount of the specimen which has been dispensed, and disposed at a second distance from a rotational center of a rotary motion and at a first distance from the first channel, and (ii) a second quantification chamber connected to the dispensing chamber and the first quantification chamber, configured to hold a specific amount of the specimen which has been dispensed, and disposed at a fourth distance which is larger than the second distance from the rotational center of the rotary motion and at a third distance which is larger than the first distance from the first channel; and
 a plurality of measurement chambers each connected to the first quantification chamber and the second quantification chamber via a second channel, and configured to react the specimen with a biochemical analysis reagent, wherein:
 the dispensing chamber is fan-shaped in plan view,
 the fan-shaped dispensing chamber includes a first end and a second end at respective end portions on respective sides of the fan-shaped dispensing chamber,
 the first end is disposed at a distance from the first channel, and the second end is disposed at a distance from the first channel that is larger than the distance from the first channel at which the first end is disposed,
 the fan-shaped dispensing chamber is defined such that a radial length of the first end from the rotational center of the rotary motion is shorter than a radial length of the second end from the rotational center of the rotary motion, and
 the quantification chambers are disposed radially outward from the dispensing chamber so that a distance from the center of the rotary motion increases in stages for each of the quantification chambers.

2. The biosensor chip according to claim 1,
 further comprising an overflow chamber,
 wherein the overflow chamber is disposed at a distance from the first channel that is larger than the third distance,
 wherein the overflow chamber is configured to hold any specimen that overflows from the first quantification chamber and the second quantification chamber during the rotary motion.

3. The biosensor chip according to claim 2,
 wherein the overflow chamber is disposed at a distance from the rotational center of the rotary motion that is larger than the fourth distance.

* * * * *